(12) United States Patent
Flohr et al.

(10) Patent No.: US 6,504,893 B1
(45) Date of Patent: Jan. 7, 2003

(54) METHOD FOR EXAMINING A BODY REGION EXECUTING A PERIODIC MOTION

(75) Inventors: Thomas Flohr, Uehlfeld (DE); Bernd Ohnesorge, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/724,057

(22) Filed: Nov. 28, 2000

(30) Foreign Application Priority Data

Nov. 28, 1999 (DE) .......................... 199 57 082

(51) Int. Cl.[7] ................................ A61B 6/00

(52) U.S. Cl. .................. 378/8; 378/15; 378/94

(58) Field of Search ................... 378/4, 8, 15, 91, 378/94, 110, 112, 113, 115

(56) References Cited

U.S. PATENT DOCUMENTS

| 5,485,494 A | | 1/1996 | Williams et al. |
| 5,625,662 A | | 4/1997 | Toth et al. |
| 5,751,782 A | * | 5/1998 | Yoshitome ................. 378/98.5 |
| 5,832,051 A | * | 11/1998 | Lutz ............................... 378/8 |
| 5,991,356 A | * | 11/1999 | Horiuchi et al. ............... 378/8 |
| 6,275,560 B1 | * | 8/2001 | Blake et al. .................... 378/8 |
| 6,298,111 B1 | * | 10/2001 | Ozaki ............................ 378/8 |

* cited by examiner

Primary Examiner—David P. Porta
Assistant Examiner—Therese Barber
(74) Attorney, Agent, or Firm—Schiff Hardin & Waite

(57) ABSTRACT

In a method for examining a body region of an examination subject executing a periodic motion with a CT apparatus having a multi-line detector system in spiral mode, the X-ray source is activated and deactivated for the emission of X-rays substantially synchronously with the periodic motion so that the X-ray source is activated only during a phase of the periodic motion to be imaged with the CT apparatus.

18 Claims, 2 Drawing Sheets

METHOD FOR EXAMINING A BODY REGION EXECUTING A PERIODIC MOTION

BACKGROUND OF THE INVENTION

The present invention is directed to a method for examining a body region executing a periodic motion in an examination subject be means of computed tomography (CT) apparatus of the type having an X-ray source continuously rotating around a system axis and from which an X-ray beam penetrating the examination subject proceeds, and having a detector system for the X-rays emanating from the X-ray source that has at least a first detector line and a last detector line, wherein the examination subject, and the X-ray source and the detector system, are displaced relative to one another in the direction of the system axis during the rotation of the X-ray source, and wherein a tomogram of at least the body region executing the periodic motion is determined with an electronic calculating means from the output data of the detector system corresponding to the detected X-rays.

DESCRIPTION OF THE PRIOR ART

The technique of prospectively ECG-triggered exposure of individual slices with single-line CT apparatus of the $3^{rd}$ generation (X-ray source and detector system rotate in common around a system axis) has been known since the early 1980's. A characteristic feature of the ECG signal, for example the R-wave, is used to implement an axial exposure in a defined heart phase for a fixed position (z-position) of the examination subject relative to the X-ray source and detector system in the direction of the system axis (z-direction). A full-revolution scan or sub-revolution scan is triggered after a selectable time delay (in % of the average RR interval of the ECG signal or absolutely in msec) relative to the respectively preceding R-wave. The data required for the image reconstruction at this z-position can be collected in a number of successive revolutions in order to improve the time resolution.

Given a single-line CT apparatus, i.e. a CT apparatus whose detector system is a single line of individual detectors, it is also known to implement a spiral scan with the ECG signal registered in parallel therewith (referred to as retrospective gating). Here, tomograms are subsequently calculated in the image reconstruction only from data in permitted data regions (in the respectively desired heart phase, for example in the diastole). In a single-line CT apparatus, this has the drawback that a gap-free coverage of the volume z-direction with tomograms is not achieved. In a spiral scan, a relative displacement of the X-ray source and detector system and the examination subject in the z-direction ensues simultaneously with a continuous rotation of X-ray-source and detector system around the system axis.

With the introduction of new CT apparatuses of the $3^{rd}$ generation with sub-second rotation, i.e. X-ray source and detector system need less than one second for a complete revolution around the system axis, and multi-slice technology, i.e. a detector system with more than one line of individual detectors, heart diagnostics with CT apparatuses is experiencing a new boom. ECG-triggered axial exposures as well as spiral exposures with ECG signal registered in parallel (retrospective ECG gating) have been expanded to multi-slice CT apparatuses, i.e. CT apparatuses with multi-slice technology, which are also referred to as multi-line CT apparatuses. Due to the multi-cell quality, new possibilities also exist in retrospectively gated spiral examination with suitable reconstruction techniques such as, for example, the gap-free presentation of the heart volume in the z-direction in any desired phase of the heart cycle.

In ECG-triggered axial exposures, radiation is only triggered within the time span during which the data actually required for the image reconstruction are registered. The method is thus dose-sensitive; it uses only the X-ray dose actually needed for the image calculation. However, one tomogram of a slice (given single-line CT apparatus) or a number of tomograms of slices (given multi-line CT apparatus) are respectively registered at fixed table positions per exposure (scan). Between two scans, the examination subject and the X-ray source and the detector system—which assume a fixed z-position relative to one another during a scan—must be brought into the new, desired z-position. This takes time and is the reason that tomograms usually cannot be registered in every heart cycle (heart period) but only in every second or every third. The examination time is considerably lengthened as a result, and it is often not possible to acquire tomograms of the desired, thin slices of the entire heart volume in one breath-holding phase. Given multi-slice CT apparatus, moreover, the tomograms arise automatically at the spacing of a detector line in z-direction. For qualitatively high-grade 3D applications, for example volume renderings for presentation of the coronary arteries, however, tomograms with a smaller spacing in the z-direction are required. A reconstruction of corresponding tomograms is not possible given conventional single-slice exposures.

Given spiral scans with a multi-line CT apparatus having the ECG signal registered in parallel, data are registered during the entire duration of the spiral scan. The data registered in the desired heart phases of the heart cycle are identified later (retrospectively) from the ECG signal registered during the spiral scan and are utilized for the reconstruction. In a multi-slice CT apparatus, this method has the advantage that tomograms in every desired heart phase can be reconstructed overlapping in the z-direction at arbitrarily small spacings. Due to the continuous relative motion between the examination subject and the X-ray source and detector system, the coverage of the entire heart volume with thin slices is possible in one breath-holding phase in a multi-slice CT apparatus. Both features are preconditions for qualitatively high-grade 3D representations of the heart.

In such exposure techniques, the patient absorbs an X-ray dose that is not inconsiderable.

In the context of reducing the dose applied to a patient, U.S. Pat. No. 5,625,662 teaches modulating the tube current of an X-ray tube provided as the X-ray source in a CT apparatus, dependent on the rotational angle of the X-ray tube as well as on weighting factors to be applied to the data acquired at the respective rotational angle.

In the same context, U.S. Pat. No. 5,485,494 discloses a CT apparatus wherein the tube current of an X-ray tube provided as the X-radiation source is modulated dependent on the rotational angle, this modulation being undertaken according to a stored function that is preferably acquired on the basis of a test scan of the patient.

SUMMARY OF THE INVENTION

An object of the present invention is to provide a method of the type initially described, wherein a body region of an examination subject executing a periodic motion can be registered with a reduced radiation dose.

The above object is achieved in accordance with the principles of the present invention in a method for examining a body region of an examination subject executing a periodic motion with a CT apparatus having a multi-line detector system in spiral mode, wherein the X-ray source is activated and deactivated for the emission of X-rays substantially synchronously with the periodic motion, so that the X-ray source is activated only during a phase of the periodic motion to be imaged with the CT apparatus.

In the invention, thus, the advantages of a prospective triggering (only the dose actually required is applied) are united with the advantages of the spiral scan with a multi-line CT apparatus (gap-free volume coverage, possibility of overlapping reconstruction of tomograms) for examinations of, for example, the heart in a previously defined (selected) heart phase. To that end, full revolution or sub-revolution scans are prospectively triggered during the individual heart cycles with a selectable time delay relative to the respectively preceding R-wave of the ECG signal (in % or as a fraction of the average duration of the R R interval of the ECG signal or absolutely in msec), with X-rays being emitted only during the time for the registration of the data during the full revolution or sub-revolution scan, with the detector system comprising a number of detector lines (multi-line full revolution datasets or sub-revolution datasets). Thus, not only the data registration but also the X-rays are prospectively triggered, with the X-ray source being correspondingly activated and deactivated. The relative displacement in the z-direction between the examination subject and the X-ray source and detector system is not arrested in the "stop and go" operation for the respective scan and undertaken only from one z-position to the next between two scans as in spiral scans. Instead, the relative displacement ensues continuously during the scans as well as in the time between them. Multi-line sub-revolution data or full revolution data are thus obtained wherein each projection corresponds to a different z-position. By applying suitable reconstruction and weighting methods (for example, projection-dependent weighting between the data of the individual detector lines), gap-free tomograms can be reconstructed therefrom in the z-direction within a region that is dependent on the feed velocity, and thus on the pitch. The feed velocity is selected dependent on the period duration of the heart cycles, i.e. on the heart frequency, taking the detector width into consideration such that the regions covered by successive datasets overlap in the z-direction or—in the limit case—abut one another gap-free. The entire heart volume thus can be scanned in one breath-holding phase due to the continuous relative displacement in the z-direction between the examination subject and the X-ray source and detector system, and due to the elimination of the acceleration and deceleration phases required given discontinuous displacement.

The method of adapting the feed velocity to the heart frequency is relevant not only to the inventive method but also to conventional ECG-gated multi-line CT spiral scans.

In a version of the invention, the time duration during which the X-ray source is activated during a heart cycle is longer than the duration of a time interval during which measured data are acquired, i.e. it is longer than the duration of a reconstruction interval or data interval. In the case of fluctuations of the duration of the heart cycle (arrhythmia) it is thus assured that the phase of the heart cycle to be image is in fact registered.

In another version of the invention, the time curve of the ECG signal and the measured data are stored, and the measured data utilized for determining a tomogram are selected, taking the signal into consideration, so that they were acquired during the phase to be imaged. A retrospective ECG-gating thus can also be implemented on the basis of the inventive method.

It is thus clear that, when there is interest only for tomograms of the heart in a specific phase, usually the quiescent phase (diastole), the inventive method is clearly more dose-sensitive than a spiral scan with retrospective gating implemented with a multi-line CT apparatus, since the patient is irradiated with X-rays during the entire spiral scan in the latter case but only a small part of the registered data is in fact used for the image reconstruction.

DESCRIPTION OF THE PREFERRED EMBODIMENTS

Figure 1:
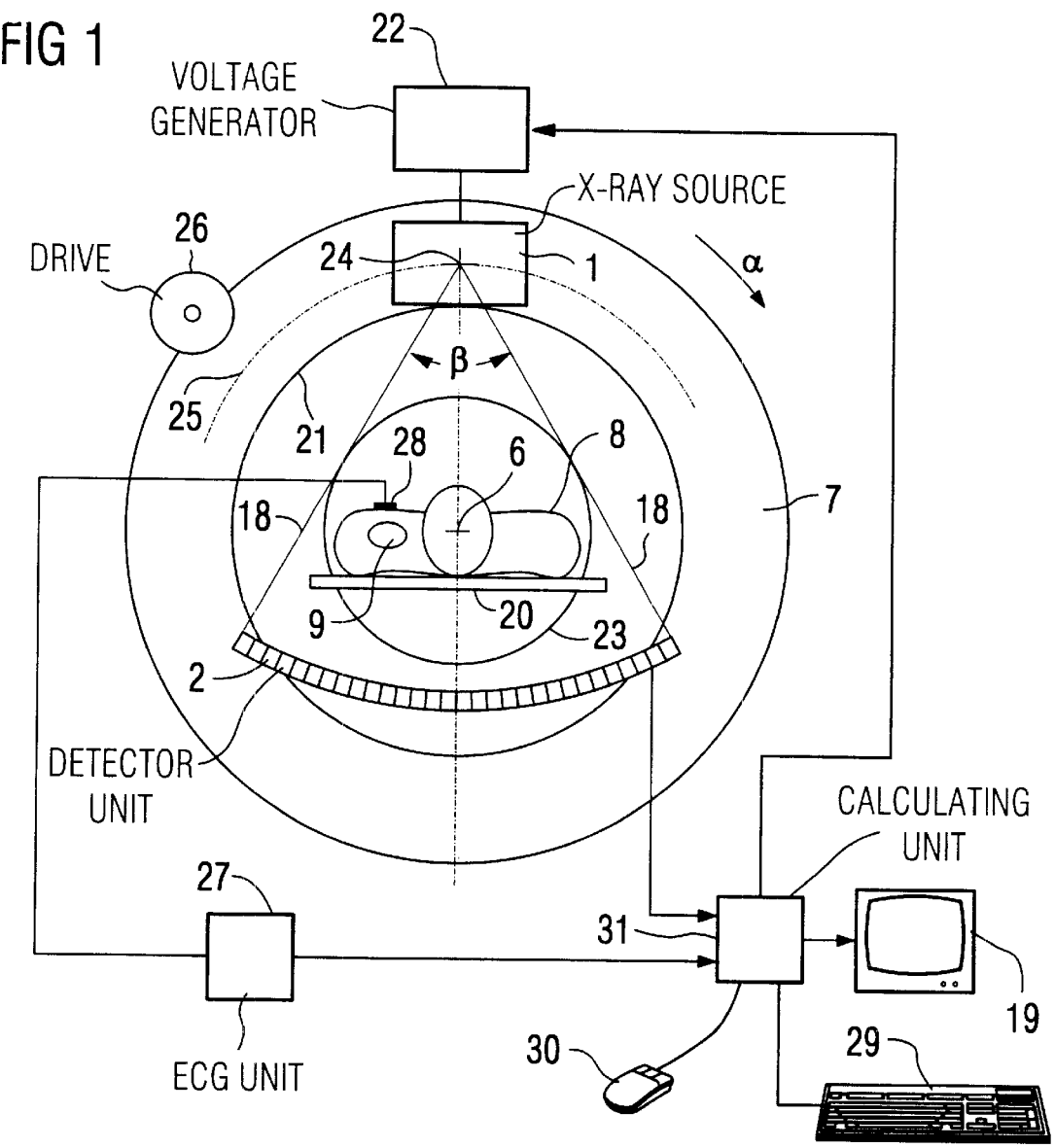
FIG. 1 is a block diagram of a CT apparatus for implementation of the inventive method.
Figure 2:
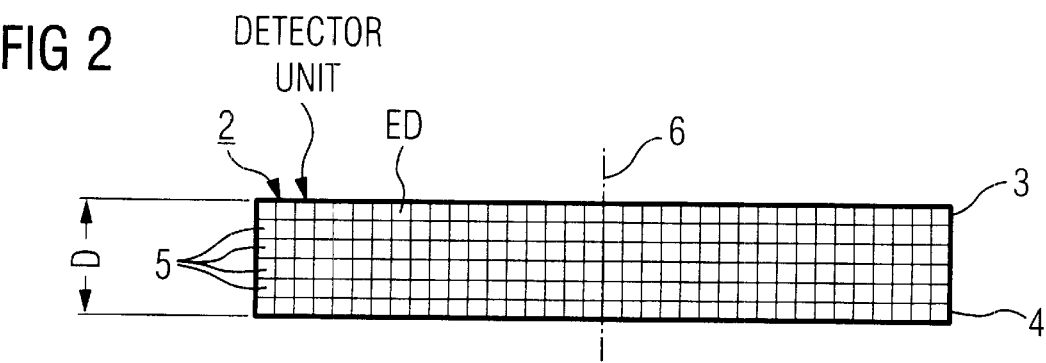
FIG. 2 shows the detector unit of the CT apparatus of FIG. 1.

FIGS. 1 and 2 schematically show a CT apparatus for the implementation of the inventive method.

The CT apparatus has a measuring unit composed of an X-ray source 1 that emits an X-ray beam 18, and a detector unit 2 that is composed of a number of lines of individual detectors, for example 512 individual detectors per line, with the lines following one another in the direction of a rotational axis. The focus of the X-ray source 1 from which the X-ray beam 18 proceeds is referenced 24. The examination subject—a human patient 8 in the illustrated exemplary embodiment—lies on a positioning table 20 that extends through the measurement opening 21 of an annular carrier 7, referred to as the gantry.

As shown in FIG. 2, the detector unit 2 has a first detector line 3 and a last detector line 4. One or—as shown—more further detector lines 5 can be arranged between the first and the last detector lines 3, 4.

The detector lines 3 through 5 proceed at a right angle relative to the rotational axis 6, which is indicated dot-dashed in FIG. 2. The first detector line 3 and the last detector line 4 are spaced from one another by a detector width D parallel to the rotational axis 6. The detector width D is measured from line middle to line middle.

The X-ray source 1 and the detector unit 2 are attached to the carrier 7 opposite one another such that the X-ray beam 18 emanating from the X-ray source 1 strikes the detector unit 2. The carrier 7 is mounted to be rotatable around the rotational axis 6 of the CT apparatus, which represents the system axis, and rotates with a speed n around the rotational axis 6 for scanning the patient 8. The X-ray beam 18 proceedings from the X-ray source 1 operated with a voltage generator 22, thus covers a measurement field 23 having a circular cross-section. The focus 24 of the X-ray source 1 moves on a focus path 25 curved circularly around a rotational center lying on the rotational axis 6.

The X-ray beam 18 transirradiates the patient 8, and the X-rays arriving at the detector unit 2 are detected during the rotation at a number of projection angles α, and the output data of the individual detectors for each of the detector lines 3 through 5 are combined to form a projection belonging to the respective projection angle α. A number of projections corresponding to the number of detector lines 3 through 5 thus belongs to each projection angle α.

Using the projections registered during a reconstruction interval, which can cover a number of data intervals and that proceed from the detector unit 2 to an electronic calculating unit 31, the calculating unit 31 reconstructs a tomogram of a subject under examination on the basis of known algorithms. In order to be able to meaningfully reconstruct tomograms of the subject under examination, the registration of projections is required at successive projection angles α that extend over a reconstruction interval that must be equal to at least 180°+β, whereby β is the aperture angle of the X-ray beam 18 shown in FIG. 1, also referred to as the fan angle.

As mentioned, the drive 26 allocated to the carrier 7 is designed to allow the carrier 7 to rotate continuously. A further drive (not shown) is also provided that enables a relative displacement of the positioning table 20, and thus of the patient and the carrier 7, and the measuring unit 1, 2 in the direction of the rotational axis 6 with a feed velocity v.

There is thus the possibility of scanning three-dimensional regions of the patient 8 in the form of a spiral scan by continuously rotating the carrier 7 with the measuring unit 1, 2 while a relative displacement of positioning table 20 and the carrier 7 in the direction of the rotational axis simultaneously ensues with a feed velocity v.

For the implementation of examinations of the heart or of heart-proximate regions of the body of the patient 8 moving in the rhythm of the heart action, the CT apparatus according to FIG. 1 also has a known ECG unit 27 that can be connected to the patient 8 via electrodes (one thereof being shown in FIG. 1 and being referenced 28) and that serves for the acquisition of the ECG signal of the patient 8 parallel to the examination with the CT apparatus. Data, preferably digital data, representing the ECG signal are supplied to the electronic calculating means 31.

Insofar as possible, the electrodes of the ECG unit 27 are applied to the body of the patient so that they do not negatively affect the examination of the patient 8.

A keyboard 29 and a mouse 30 that enable the operation of the CT apparatus are connected to the electronic calculating unit 31.

Insofar as body portions of the patient 8 that can be placed at rest are to be registered, no noteworthy problems arise for the registration of the projections. By contrast, the registration of projections of a periodically moving subject is problematical unless further steps are taken. An example of such a moving subject is the human heart 9, which is schematically shown in FIG. 1.

As is known, the human heart 9 essentially executes a periodic motion. The periodic motion is composed of an alternating sequence of a quiescent or relaxation phase and a motion or beating phase. The quiescent phase has a duration between—usually—500 through 800 ms and the beating phase has a duration of 200 through 250 ms.

The speed n of the carrier 7 usually lies at 45 through 120 revolutions per minute. By comparing the speed n to the duration of the quiescent phase of the heart 9, thus, it can be easily determined that the carrier 7 rotates during the quiescent phase of the heart 9 by a rotational angle γ that lies between 135° (500 ms at 45 rpm) and 576° (800 ms at 120 rpm).

When the speed n is selected high enough, the carrier 7 rotates through an angle during the respective phase of a heart cycle to be registered, for example during a quiescent phase, that is greater than the required reconstruction interval. It is thus possible to register the projections required for the reconstruction of a tomogram of the registered heart 9 region during the respective phase of a heart cycle to be registered.

If the heart frequency is so high that it is not possible to register the projections belonging to a complete reconstruction interval during a single heart cycle, this registration can ensue during the desired phase in a number of successive heart cycles. The reconstruction interval is then composed of a number of data intervals that belong to different heart cycles.

As already mentioned, the electrocardiogram (ECG) of the human heart 9 is registered in parallel in order to be able to identify the quiescent phases 13 of the human heart therefrom.

In the inventive method, the ECG signal is used in order to activate and deactivate the X-ray source 1, for example an X-ray tube, so that it only emits X-rays during the respective phase of a heart cycle to be registered, for example during the quiescent phase of the heart 9. This is performed by the electronic calculating unit 31 connected to the generator means 22.

In this way, the radiation load on the patient 8 is reduced, since the application of X-rays is limited to those time intervals, namely the reconstruction or data intervals, wherein projections that can be used for the image reconstruction are registered.

Figure 3:
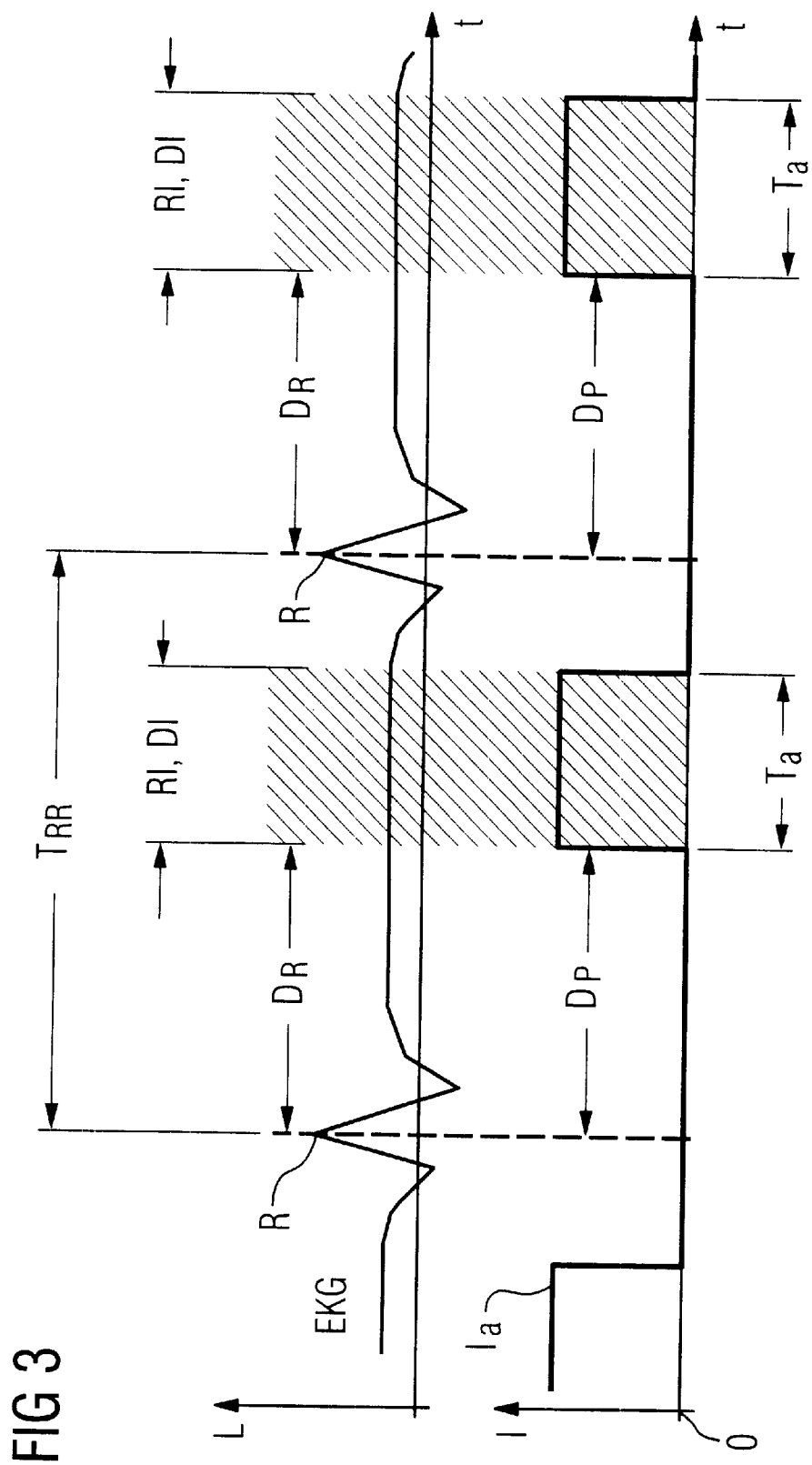
FIG. 3 is a diagram illustrating the functioning of the inventive method.

This can be seen from FIG. 3 wherein the level L of the ECG signal (referenced ECG) of a patient and the intensity I of the X-radiation emanating from the X-ray source 1 are entered above one another over the time t. The ECG signal illustrates the periodic motion of the heart of the patient, with the beginning of a heart cycle being defined by the RR interval $TR_{RR}$, i.e. the distance of the R-wave initiating the respective heart cycle from the R-wave initiating the following heart cycle. The quiescent phase of the heart to be registered in the illustrated example is indicated hatched.

As can be seen from the curve of the intensity I of the X-rays, which changes between zero and the activation value $I_a$, the X-ray source 1 is activated and deactivated so that it is only activated during the heart phase to be registered, i.e. the quiescent phase.

This occurs in that the X-ray source 1 is, so to speak, prospectively activated a respective delay time $D_P$ after the occurrence, being activated for a time duration $T_a$.

The time duration $T_a$ during which projections are registered for a full revolution scan or sun-revolution scan can be a complete reconstruction interval RI, or only a data interval DI.

The electronic calculating unit 31 calculates the delay time $D_P$ and the time duration $T_a$ by determining the average of the duration of the RR intervals $T_{RR}$ from a preselectable number of preceding RR intervals and determines the delay time $D_P$ and the time duration $T_a$ therefrom as preselectable percentages or fractions of this average value. Alternatively, the delay time $D_P$ and the time duration $T_a$ can also be preselected as time durations, for example in milliseconds.

Taking the average of the duration of the RR intervals $T_{RR}$ from a preselectable number of preceding RR intervals into consideration, the electronic calculating unit 31 sets the feed velocity v so that the displacement of the positioning table 20 in the direction of the system axis 6, i.e. the displacement of the measuring unit 1, 2 and of the patient 8 relative to one another in the direction of the system axis 6, that occurs during a reconstruction interval RI or data interval DI, does not exceed a detector width D (see FIG. 2). The regions of the patient 8 covered by successive reconstruction intervals RI or data intervals DI thus overlap in the direction of the system axis 6 or adjoin one another gap-free. The entire volume of the patient 8 scanned in the direction of the system axis thus can be covered gap-free with tomograms.

Moreover, there is also the possibility of retrospectively extracting the projections belonging to a reconstruction interval from the registered projections when the projections and the ECG signal are stored. This is illustrated in FIG. 3 by indicating a time interval $D_R$ that is determined by the electronic calculating means 31 analogous to the delay time $D_P$.

In summary, the inventive method has the following significant features.

The inventive method provides an exposure technique for volume heart and lung examinations with multi-line CT apparatus wherein the patient bed moves continuously as in spiral scans but, differing from spiral scans, radiation is not continuous but is prospectively triggered with a freely selectable time shift relative to the respectively preceding R-wave of the ECG signal—for example, full revolution or sub-revolution multi-line CT scans—so that radiation is only applied and data registered during the duration of the full revolution scan or sub-revolution scan.

An adaptation of the feed velocity of the bed to the heart frequency ensues, so that the z-intervals (in the direction of the longitudinal patient axis) covered by time-successive, prospectively triggered full revolution or sub-revolution multi-line CT data overlap or adjoin one another gap-free, so that the entire examination volume is covered gap-free.

The inventive method also enables an adaptation of the feed velocity of the bed to the heart frequency for retrospectively ECG gated spiral scans.

Instead of the ECG signal, other physiological parameters or signals can be employed to provide the information about the respective phase of the heart cycle, for example heart wall motion or stethoscopic heart beat analysis.

The invention is explained above with reference to the example of heart examinations, however, other periodically moving body regions can be examined with the inventive method.

A CT apparatus of the third generation is employed in conjunction with the above description of the invention, i.e. the X-ray source and the detector unit are displaced in common around the system axis during the image generation. The invention, however, also can be employed in conjunction with CT apparatuses of the fourth generation wherein only the X-ray source is displaced around the system axis and interacts with a stationary detector ring, insofar as the detector ring has a plurality of detector lines. In addition to being employed in computed tomography, the invention can also be utilized in other imaging methods that operate with penetrating radiation.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A method for examining a body region executing a periodic motion in an examination subject by conducting a spiral scan in a computed tomography apparatus having a system axis, said method comprising the steps of:

providing an X-ray source, which emits an X-ray beam, and a multi-line radiation detector on which said X-ray beam is incident, said multi-line radiation detector having multiple lines of detector elements, said lines being disposed side-by-side along said system axis;

rotating said X-ray source and said radiation detector around a system axis while producing a continuous relative displacement along said system axis between said X-ray source and said radiation detector, and said examination subject, to irradiate a body region of said examination subject executing a periodic motion from a plurality of different projection angles, to obtain projection data during an acquisition time;

activating said X-ray source, for a time interval which is longer than said acquisition time, and deactivating said X-ray source during said continuous relative displacement, with X-rays being emitted by said X-ray source only during activation of said X-ray source, substantially synchronously with said periodic motion, so that said X-ray source is activated only during a selected phase of said periodic motion; and producing a computed tomogram of said region from said projection data.

2. A method as claimed in claim 1 comprising disposing said examination subject relative to said X-ray source and said radiation detector to produce a tomogram of a lung of said examination subject executing said periodic motion.

3. A method as claimed in claim 1 comprising disposing said examination subject relative to said X-ray source and said radiation detector to produce a tomogram of a heart of said examination subject executing said periodic motion.

4. A method as claimed in claim 3 comprising obtaining an ECG signal from said examination subject and controlling activation and deactivation of said X-ray source dependent on said ECG signal.

5. A method for examining a body region executing a periodic motion in an examination subject by conducting a spiral scan in a computed tomography apparatus having a system axis, said method comprising the steps of:

providing an X-ray source, which emits an X-ray beam, and a multi-line radiation detector on which said X-ray beam is incident, said multi-line radiation detector having multiple lines of detector elements, said lines being disposed side-by-side along said system axis, said multi-line detector having a first detector line and a second detector line spaced from each other by a detector width in a direction along said system axis;

rotating said X-ray source and said radiation detector around a system axis while producing a continuous relative displacement along said system axis between said X-ray source and said radiation detector, and said examination subject, to irradiate a body region of said examination subject executing a periodic motion from a plurality of different projection angles, to obtain projection data, said displacement of said X-ray source and said radiation detector, and said examination subject, relative to each other along said system axis occurring with a feed velocity so that displacement occurring during a time interval during which said projection data are acquired does not exceed said detector width;

activating and deactivating said X-ray source during said continuous relative displacement, with X-rays being emitted by said X-ray source only during activation of said X-ray source, substantially synchronously with said periodic motion, so that said X-ray source is activated only during a selected phase of said periodic motion; and producing a computed tomogram of said region from said projection data.

6. A method as claimed in claim 5 comprising disposing said examination subject relative to said X-ray source and said radiation detector to produce a tomogram of a lung of said examination subject executing said periodic motion.

7. A method as claimed in claim 5 comprising disposing said examination subject relative to said X-ray source and said radiation detector to produce a tomogram of a heart of said examination subject executing said periodic motion.

8. A method as claimed in claim 7 comprising obtaining an ECG signal from said examination subject and controlling activation and deactivation of said X-ray source dependent on said ECG signal.

9. A method for examining a body region executing a periodic motion in an examination subject by conducting a spiral scan in a computed tomography apparatus having a system axis, said method comprising the steps of:

providing an X-ray source, which emits an X-ray beam, and a multi-line radiation detector on which said X-ray beam is incident, said multi-line radiation detector having multiple lines of detector elements, said lines being disposed side-by-side along said system axis;

rotating said X-ray source and said radiation detector around a system axis while producing a continuous relative displacement along said system axis between said X-ray source and said radiation detector, and said examination subject, to irradiate a body region of said examination subject executing a periodic motion from a plurality of different projection angles, to obtain projection data;

obtaining a signal from said examination subject representing said periodic motion;

activating and deactivating said X-ray source during said continuous relative displacement by, activating said X-ray source at a first delay time after a beginning of a period of said motion represented by said signal, and deactivating said X-ray source after a second delay time after a beginning of said period, said first delay time being shorter than said second delay time with X-rays being emitted by said X-ray source only during activation of said X-ray source, substantially synchronously with said periodic motion, so that said X-ray source is activated only during a selected phase of said periodic motion; and producing a computed tomogram of said region from said projection data.

10. A method as claimed in claim 9 wherein said signal has a time curve, and comprising the steps of storing said time curve and said projection data and identifying data in said projection data, relative to said time curve, which were acquired during said selected phase and producing said tomogram only using said data which occurred during said selected phase.

11. A method as claimed in claim 9 comprising disposing said examination subject relative to said X-ray source and said radiation detector to produce a tomogram of a lung of said examination subject executing said periodic motion.

12. A method as claimed in claim 9 comprising disposing said examination subject relative to said X-ray source and said radiation detector to produce a tomogram of a heart of said examination subject executing said periodic motion.

13. A method as claimed in claim 12 comprising obtaining an ECG signal from said examination subject and controlling activation and deactivation of said X-ray source dependent on said ECG signal.

14. A method for examining a body region executing a periodic motion in an examination subject by conducting a spiral scan in a computed tomography apparatus having a system axis, said method comprising the steps of:

providing an X-ray source, which emits an X-ray beam, and a multi-line radiation detector on which said X-ray beam is incident, said multi-line radiation detector having multiple lines of detector elements, said lines being disposed side-by-side along said system axis;

rotating said X-ray source and said radiation detector around a system axis while producing a continuous relative displacement along said system axis between said X-ray source and said radiation detector, and said examination subject, to irradiate a body region of said examination subject executing a periodic motion from a plurality of different projection angles, to obtain projection data;

obtaining a signal from said examination subject representing said period motion, and identifying an average duration of a period of said signal;

activating and deactivating said X-ray source during said continuous relative displacement by, activating said X-ray source at a time corresponding to a first fraction of said average duration after a beginning of a period, and deactivating said X-ray source at a time corresponding to a second fraction of said average duration following said beginning of said period, said first fraction being smaller than said second fraction with X-rays being emitted by said X-ray source only during activation of said X-ray source, substantially synchronously with said periodic motion, so that said X-ray source is activated only during a selected phase of said periodic motion; and producing a computed tomogram of said region from said projection data.

15. A method as claimed in claim 14 wherein said signal has a time curve, and comprising the steps of storing said time curve and said projection data and identifying data in said projection data, relative to said time curve, which were acquired during said selected phase and producing said tomogram only using said data which occurred during said selected phase.

16. A method as claimed in claim 14 comprising disposing said examination subject relative to said X-ray source and said radiation detector to produce a tomogram of a lung of said examination subject executing said periodic motion.

17. A method as claimed in claim 14 comprising disposing said examination subject relative to said X-ray source and said radiation detector to produce a tomogram of a heart of said examination subject executing said periodic motion.

18. A method as claimed in claim 17 comprising obtaining an ECG signal from said examination subject and controlling activation and deactivation of said X-ray source dependent on said ECG signal.

* * * * *